United States Patent [19]

Sturman

[11] Patent Number: 4,559,808
[45] Date of Patent: Dec. 24, 1985

[54] GAS/LIQUID SEPARATOR AND ATOMIZATION CELL

[75] Inventor: Barry T. Sturman, Mulgrave, Australia

[73] Assignee: Varian Techtron Pty Limited, Mulgrave, Australia

[21] Appl. No.: 695,581

[22] Filed: Jan. 28, 1985

[30] Foreign Application Priority Data

Feb. 3, 1984 [AU] Australia ............... PG 3458/84

[51] Int. Cl.⁴ .......................................... G01M 31/00
[52] U.S. Cl. .................................... 73/23; 73/863.21;
55/270; 55/18; 55/462; 422/81; 422/101; 436/177
[58] Field of Search ..................... 55/270, 67, 462, 18,
55/391, 392; 73/863.21, 23; 250/288; 422/68,
81, 88, 91, 101; 436/177, 168

[56] References Cited

U.S. PATENT DOCUMENTS

| 2,732,033 | 1/1956 | Parks | 55/391 |
| 2,967,764 | 1/1961 | Skeggs | 55/462 |
| 3,449,584 | 6/1969 | Bailey | 73/23 |
| 3,834,493 | 9/1974 | Hubert | 55/462 |
| 4,330,385 | 5/1982 | Arthur et al. | 73/23 |
| 4,528,158 | 7/1985 | Giles et al. | 422/68 |

FOREIGN PATENT DOCUMENTS 1248898 11/1960 France ................... 55/391

Primary Examiner—Bernard Nozick
Attorney, Agent, or Firm—Stanley Z. Cole; Edward H. Berkowitz

[57] ABSTRACT

A method and apparatus for separating the liquid and gas components of a liquid/gas stream and particularly for use in chemical analysis systems such as atomic absorption spectrophotometry. The liquid/gas stream is introduced into a separation chamber so as to impact against an upstanding tube located within that chamber and the surface of which is treated to encourage adhesion thereto of the liquid component. An enlargement of the tube above the zone of impact minimizes carry-over of spray to the upper region of the chamber. The liquid/gas stream includes the sample to be analyzed together with a quantity of carrier gas, and a further quantity of carrier gas is introduced into the upper region of the chamber through the aforementioned tube. A gas exhaust opening is provided at the top of the chamber.

28 Claims, 2 Drawing Figures

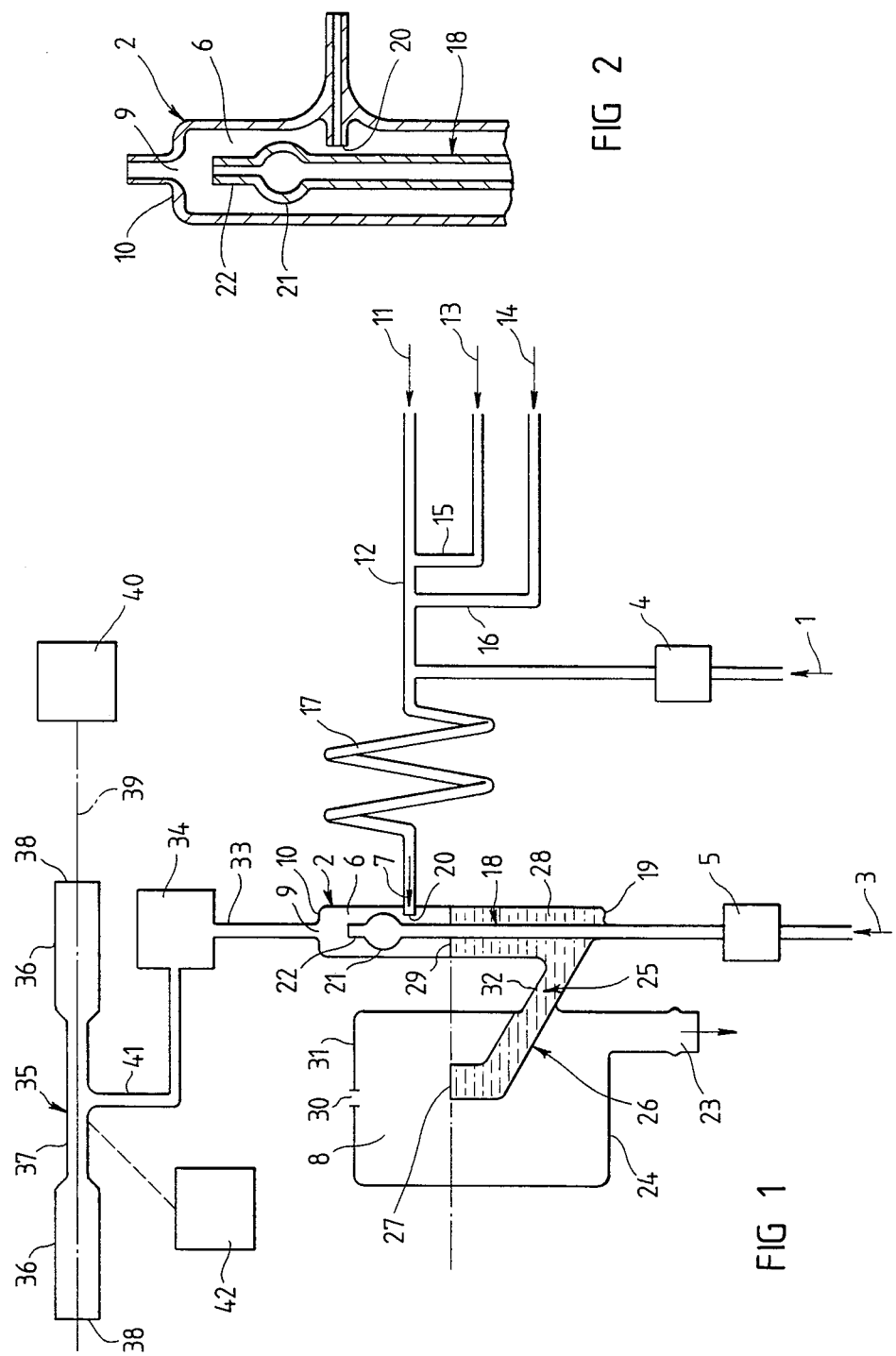

GAS/LIQUID SEPARATOR AND ATOMIZATION CELL

This invention relates to chemical analysis of elements such as arsenic, antimony, bismuth, seleniun, tellurium, germanium, tin, lead and mercury. The invention is particularly concerned with analysis techniques such as atomic absorption spectrophotometry in which a gaseous hydride or vapour of such an element is generated for the purpose of the analysis step. The invention is also useful in systems involving the generation of ammonia gas or some other gas for analysis by molecular absorption spectrophotometry.

It is known to generate a hydride, vapour or gas of the foregoing kind (hereinafter simply called the sample gas) by reaction of a liquid sample with an appropriate acid and reducing agent in a continuous flow system. Separation of the sample gas from the liquid body is carried out in a suitable vessel and it is known to aid that separation by introducing a carrier gas into the vessel or into the sample gas/liquid stream prior to entry of that stream into the vessel.

A problem with such prior systems is that the carrier gas tends to become saturated with water vapour which may condense and thereby disturb the precision of the analysis measurement. Attempts have been made to meet that problem by introducing a second stream of "dry" carrier gas into the apparatus between the separator vessel and the analytical instrument, but that has the disadvantage of diluting the sample gas and thereby reduces the sensitivity of the analysis measurement.

It is one object of the present invention to provide an improved method and apparatus for separating the sample gas and liquid. It is a further object of the invention to provide such a method and apparatus which avoids or minimizes condensation of water in the conduit connecting the separator to the analytical instrument. Still another object of the invention is to provide such a method and apparatus which is controllable to achieve maximum signal to noise ratio in the output of the analytical instrument.

In chemical analysis of the foregoing kind, the sample gas is decomposed in a heated cell located in the path of an optical beam. That cell may take any of several forms, but a preferred form of the present invention is particularly concerned with such cells in the form of a tube heated by an external energy source such as a flame or electrical means. Such tubes are generally cylindrical and in use the tube is arranged so that the optical beam of the spectrophotometer passes along its axis.

A problem with atomization tubes of the foregoing kind is that the optical beam is typically composed of two coaxial cones having a common apex at a focal point located within the tube. The resulting converging-diverging nature of the beam is not wholly compatible with the cylindrical nature of the tube bore so that the beam is either partially obstructed by the tube ends or the tube encloses a significant volume of space through which the beam does not pass. Obstruction of the beam has the disadvantage of increasing the photon noise component in the analytical response. On the other hand, the inclusion of space within the tube which is not traversed by the beam has the disadvantage that time and sample gas are wasted in filling that space with gas. If that space is not filled with gas, steady state conditions will not be achieved and that will result in less than optimum analytical sensitivity.

It is an object of a preferred form of the present invention to overcome or minimize the aforementioned problems in externally heated atomization tubes.

According to one aspect of the present invention there is provied a gas/liquid separator including, a separation chamber, a first inlet formed through one side of said chamber, a second inlet formed by a tube which extends into said chamber, said first and second inlets each being separately connectable to a gas source, at least an end portion of said tube extends upwardly towards an upper end of said chamber, said tube end portion is located in the path of gas entering said chamber through said first inlet, and a gas outlet formed through said chamber upper end.

According to a further aspect of the present invention there is provided a method of separating gas and liquid including the steps of: introducing a gas/liquid stream into a chamber so as to impinge against an upwardly extending tube provided in that chamber, said tube being arranged to encourage adhesion thereto of the liquid component of said gas/liquid stream, introducing carrier gas into an upper region of said chamber through said tube, and exhausting said carrier gas and the gas component of said gas/liquid stream through an upper end of said chamber.

The essential features of the invention, and further optional features, are described in detail in the following passages of the specification which refer to the accompanying drawings. The drawings however, are merely illustrative of how the invention might be put into effect, so that the specific form and arrangement of the features (whether they be essential or optional features) shown is not to be understood as limiting on the invention.

In the drawings:

FIG. 1 is a diagrammatic view of apparatus according to the invention included in a chemical analysis system, FIG. 2 is an enlarged view of portion of the apparatus shown in FIG. 1.

The method of the invention is characterized in that separation is assisted by introduction of two separate streams of carrier gas into the system. Referring to FIG. 1 of the drawings, one gas stream 1 enters the system at the inlet side of a separator vessel 2 and the other gas stream 3 enters directly into the vessel 2. It is preferred that separate flow control means 4 and 5 respectively is provided for each of the carrier gas streams 1 and 3 so that those streams may be independantly controlled. The method will be hereinafter described in greater detail with reference to the example apparatus as shown in FIG. 1 which includes features of the invention.

The separator includes the vessel 2 and that has a chamber 6 adapted to receive a gas/liquid stream 7. The chamber 6 may be cylindrical and is preferably connected at its lower end to the lower end of a second chamber 8 which, in use, functions as a constant head reservoir as hereinafter described. A gas outlet 9 is provided through the upper end 10 of the separator chamber 6 and that outlet 9 can be connected to an associated analytical instrument in any appropriate manner.

The sample 11 is fed to the separator chamber 6 through a feed conduit 12 which preferably enters the chamber 6 adjacent the upper end 10 thereof. An appropriate acid 13 and an appropriate reducing agent 14 may be introduced into the sample stream through separate conduits 15 and 16 respectively connected to the feed conduit 12, and in the arrangement shown the acid 13 is introduced before the reducing agent 14. The respective streams of the sample 11, acid 13 and reducing agent 14 combine within the feed conduit 12 to form a reaction mixture and each of those components may be introduced into the feed conduit under the influence of a pump or other feed means. A sample gas is generated out of the reaction mixture during its passage along the feed conduit 12 and hydrogen may be generated also by reaction of excess reducing agent 14 with the acidified sample liquid.

It is preferred that a coil 17 is provided in the feed conduit 12 adjacent the connection between that conduit 12 and the chamber 6. It is further preferred that the carrier gas stream 1 is introduced into the feed conduit 12 adjacent the inlet side of the coil 17 and, as previously stated, the flow rate of that gas stream 1 is controlled through a suitable constant flow device 4. In operation, the sample gas, along with hydrogen which may be present, is stripped from the liquid into the carrier gas from stream 1 during passage through the coil 17. The resulting gas/liquid stream 7 emerges from the coil 17 to enter the separator chamber 6 and the direction of entry is preferably transverse to the longitudinal axis of the chamber 6—i.e., the upright axis of the chamber 6.

The second stream 3 of carrier gas is introduced into the separator chamber 6 separate from the gas/liquid stream 7 as will be apparent from FIG. 1. The carrier gas stream 3 may be dry in nature and its flow rate is controlled through a suitable constant flow device 5 independant of that controlling the flow rate of the carrier gas stream 1. Also, the two streams 1 and 3 may emanate from the same source or different sources. In the arrangement shown the gas stream 3 is introduced into the separator chamber 6 through a tube 18 extending through the lower end 19 of the chamber 6 and arranged substantially coaxial with the chamber 6. The tube 18 extends upwardly through the chamber 6 to terminate adjacent the upper end 10 of the chamber 6 at a point above the inlet 20 through which the gas/liquid stream 7 enters the chamber 6. The tube 18 therefore lies in the path of the incoming gas/liquid stream 7 and at least part of the outer surface of the tube 18 may be roughened or otherwise treated to promote adhesion between the tube 18 and the liquid component of the impinging stream 7.

As shown in FIGS. 1 and 2 the tube is provided with an enlargement 21 at a location above the inlet 20. That enlargement 21 is preferably spherical as shown and serves to inhibit upward travel of spray generated by collision of the stream 7 with the tube 18. If desired, the outer surface of the enlargement 21 may be roughened or otherwise treated to promote adhesion of liquid, and the same may apply to the portion 22 of the tube 18 which projects above the enlargement 21.

The reservoir chamber 8 may be also cylindrical in nature and has a liquid outlet 23 extending through its lower end 24. A liquid drain 25 interconnects the two chambers 6 and 8 and in the arrangement shown that drain 25 includes a tube 26 which extends angularly upwards from the lower end 19 of the separation chamber 6 and projects into the chamber 8. The upper open end 27 of the tube 26 is located at a level below the inlet 20 whereby the gas/liquid stream 7 enters the separator chamber 6. Thus, a body of liquid 28 contained in the interconnected reservoir and separator chambers 8 and 6 has a level 29 below the inlet 20 and that level 29 is maintained constant through the operation of the drain tube 26. An opening 30 may be provided at or adjacent the top 31 of the reservoir chamber 8 to ensure that chamber 8 is always at atmospheric pressure.

Other types of reservoir and overflow control systems may be adopted, but the arrangement described above and shown in the drawings has been found satisfactory in use. A particular advantage of that arrangement is that a relatively small volume of liquid is retained within the chamber 6 and tube 26 and that facilitates flushing of the separation system between use with different samples. In addition, the slope of the tube 26 minimizes the possibility of air bubbles accumulating in the lower portion of the chamber 6 and thereby blocking or hindering transfer of liquid out of the chamber 6. It is preferred that the lower section 32 of the tube 26 which is immediately adjacent the chamber 6, has a cross sectional size smaller than the remainder of the tube 26. Such an arrangement tends to avoid the possibility of stratification occurring in the liquid body 28.

In operation, the gas component of the gas/liquid stream 7 enters the space in the separator chamber 6 above the liquid body 28 and passes from there, together with the second stream 3 of carrier gas, through the gas outlet 9 of the chamber 6. The liquid component tends to adhere to the tube 18 and flows down that tube 18 under the influence of gravity to enter the constant level liquid body 28. That provides a favourable environment for release of gas dissolved or entrained in the liquid component, and that released gas diffuses into the surrounding space to subsequently escape from the chamber 6 through the outlet 9.

The gas component of the gas/liquid stream 7 is saturated with water vapour and the second "dry" stream 3 of carrier gas mixes with that gas component to form a mixture which is not saturated with water vapour and is therefore not likely to deposit liquid water in the conduit 33 connecting that chamber 6 to the analytical instrument. If desired, an expansion chamber 34 may be located at an appropriate position in that conduit 33 as shown in FIG. 1, so as to promote mixing of the sample gas and the second stream 3 of carrier gas.

Independant control of the flow rate of the two carrier gas streams 1 and 3 allows those flow rates to be adjusted to achieve maximum signal to noise ratio in the output of the analytical instrument.

The configuration of the apparatus as described ensures relatively smooth transfer of liquid from the gas/liquid stream 7 and also inhibits transfer of liquid droplets or film to the conduit 33 connecting the separator chamber 6 to the analytical instrument. It is therefore possible to operate an analytical system having a continuous flow generation of gaseous hydrides or mercury vapour at maximum signal to noise ratio and to carry out analysis over a prolonged period of time. Furthermore, the apparatus can be constructed in a relatively compact form.

According to the particular arrangement shown, the apparatus includes a tubular atomization cell 35 having two cylindrical end portions 36 and a coaxial cylindrical central portion 37 of reduced cross section. The respective lengths of the three portions can be selected to suit particular requirements, but in the arrangement shown they are roughly of equal length. Also, the cross sectional size of each of the two end portions 36 is preferably substantially the same and the ratio between that size and the cross sectional size of the central portion 37 can be selected to suit requirements. For example, the inner diameter of the central portion 37 may be approximately one third the inner diameter of each of the end portions 36.

Such a tube configuration has the advantage that each end of the cell 35 is provided with an opening 38 of suitable size for passage of an optical beam 39 generated by a light source 40, but the space within the cell 35 to be filled by sample gas is kept to a minimum. That advantage may be optimized by providing additional steps in the tube diameter. That is, instead of having just one step each side of the axial centre of the cell 35, there may be two or more such steps so that at least one portion of different diameter intervenes between each end portion 36 and the central portion 37.

A cell 35 of the kind described can be manufatured from fused quartz or other material having the necessary characteristics of chemical, thermal and mechanical stability at the required operating temperature which may be in the range of 800° to 1200° centrigrade.

In the form shown, the ends 38 of the cell 35 are open and sample gas is introduced into the cell 35 through a conduit 41 connected to the cell 35 substantially at the longitudinal centre thereof. The sample gas therefore enters the cell 35 at its centre and emerges from each of the two open ends 38. In use, the cell 35 is aligned with the optical beam 39 of the associated instrument so that the beam 39 passes axially through the cell 35. Also, in use, the cell 35 is heated by appropriate means 42—e.g., electrical means or an external flame—to a temperature sufficient to decompose the sample gas and release atoms of the sample into the optical beam 39.

The external heating of the cell 35 may be supplemented by a combustion of hydrogen generated by reaction of gas reducing agent 14 and the acid 13. Such combustion may be supported by dissolved air from the sample 11 and reagent solutions or by oxygen or air deliberately added to the carrier gas stream 1 and/or 3.

If desired, the ends 38 of the cell 35 may be closed by windows which are transparent to the shortwave ultraviolet radiation used for analytical measurements of the kind under consideration. In that event, a suitable gas outlet (not shown) may be provided through the cylindrical wall of the cell 35 adjacent each end thereof. In a variation of such a closed end arrangement, the central gas inlet conduit 41 may be replaced by one adjacent one end of the cell 35 and the gas outlet is provided adjacent the other end.

A cell 35 as described has the advantage of being relatively convenient to align with the optical beam 39 and allows substantially uniform heating of the enclosed space. It is to be understood however, that the cell 35 may be usefully employed in situations where it is not heated, such as for example the determination of mercury according to the teaching of Tuncel and Ataman (Atomic Spectroscopy 1(4), 1 to 6, 1 to 8(1980)).

Various alterations, modifications and/or additions may be introduced into the constructions and arrangements of parts previously described without departing from the spirit or ambit of the invention as defined by the appended claims.

Having now described my invention, what I claim as new and desire to secure by Letters Patent is:

1. A gas/liquid separator including, a separation chamber, a first inlet formed through one side of said chamber, a second inlet formed by a tube which extends into said chamber, said first and second inlets each being separately connectable to a gas source, at least an end portion of said tube extends upwardly towards an upper end of said chamber, said tube end portion is located in the path of gas entering said chamber through said first inlet, and a gas outlet formed through said chamber upper end.

2. A separator according to claim 1, wherein said tube is substantially straight and extends upwardly from a lower end of said chamber, and said first inlet has an axis which extends transverse to the longitudinal axis of said tube and which lies substantially in the same plane as said longitudinal axis.

3. A separator according to claim 1, wherein at least part of said tube end portion has an outer surface which is arranged to promote adhesion of liquid to said tube and said surface is located in the path of gas entering said chamber through said first inlet.

4. A separator according to claim 1, wherein said tube end portion and said outlet are in substantial alignment.

5. A separator according to claim 1, wherein said first and second inlets are each connectable to a respective said gas source.

6. A separator according to claim 1, wherein an enlargement is provided in said tube end portion at a location above said first inlet.

7. A separator according to claim 6 wherein said enlargement is spherical in form.

8. A separator according to claim 6, wherein at least that part of the outer surface of said tube which is directly below said enlargement is treated so as to promote adhesion of liquid to that surface.

9. A separator according to claim 8, wherein said outer surface part is relatively rough.

10. A separator according to claim 1, wherein a second chamber is connected to a lower end of said separation chamber through a liquid drain.

11. A separator according to claim 10, wherein said separation chamber and said second chamber are located side by side, said second chamber has a liquid outlet, overflow means is provided to control the flow of liquid to said liquid outlet such that liquid enters said liquid outlet only when the level of liquid within said separation chamber exceeds a predetermined level, and said predetermined level is below said first inlet.

12. A separator according to claim 11, wherein said overflow means includes a tube which forms part of said liquid drain and which extends angularly upwards from the lower end of sid separation chamber to extend into said second chamber, said overflow tube has an upper open end located in the same plane as said predetermined level, and said liquid outlet is located below said upper open end.

13. A separator according to claim 12, wherein the cross sectional size of said overflow tube is least adjacent said separation chamber.

14. A separator according to claim 1, wherein a feed conduit is connected to said first inlet and is arranged to receive a sample from a sample supply, means is provided to introduce a first carrier gas stream into said feed conduit at a location between said chamber and the point of introduction of said sample into the feed conduit, and means is provided to introduce a second carrier gas stream into said tube at a location remote from said end portion thereof.

15. A separator according to claim 14, wherein each said means for introducing carrier gas includes a respective flow control device which is adjustable independant of the other said flow control device.

16. A chemical analysis apparatus and a gas/liquid separator according to claim 1.

17. Apparatus according to claim 16, wherein an atomization cell is connected to said gas outlet so as to receive gas from said outlet, and a light source is operative to direct an optical beam through said cell.

18. Apparatus according to claim 17, wherein means is provided for heating said cell.

19. Apparatus according to claim 17, wherein said cell is in the form of an elongate tube having enlarged end portions, said gas outlet is connected to an intermediate portion of said cell tube, and said cell tube is substantially coaxial with said optical beam.

20. Apparatus according to claim 17, wherein an expansion chamber is provided in the connection between said gas outlet and said cell.

21. A method of separating gas and liquid including the steps of:
   introducing a gas/liquid stream into a chamber so as to impinge against an upwardly extending tube provided in that chamber, said tube being arranged to encourage adhesion thereto of the liquid component of said gas/liquid stream,
   introducing carrier gas into an upper region of said chamber through said tube, and exhausting said carrier gas and the gas component of said gas/liquid stream through an upper end of said chamber.

22. A method according to claim 21, wherein said gas/liquid stream enters said chamber in a direction transverse to the longitudinal axis of that portion of said tube against which that stream impinges.

23. A method according to claim 21, wherein a substantially constant level of liquid is maintained in said chamber and said level is below the point of entry of said gas/liquid stream into said chamber.

24. A method according to claim 21, wherein said tube is enlarged above the zone of said gas/liquid stream impingement.

25. A method according to claim 21, wherein carrier gas is introduced into said gas/liquid stream prior to that stream entering said chamber.

26. A method according to claim 25, wherein the two said streams of carrier gas which are introduced to said chamber by way of the tube and gas/liquid stream respectively, are independantly controllable.

27. A method of analyzing a sample including the steps of: introducing a sample into a feed conduit, generating a sample gas within said conduit, introducing carrier gas into said conduit at a location such that the carrier gas enters the stream of said sample gas to form a composite gas stream, introducing said composite gas stream into a chamber so as to impinge against an upwardly extending tube provided in that chamber, said tube being arranged to encourage adhesion thereto of any liquid component of said composite gas stream, introducing carrier gas into an upper region of said chamber through said tube, and exhausting gas from said chamber through an upper end of said chamber.

28. A method according to claim 27, wherein said exhausted gas is transported to an atomization cell.

* * * * *